United States Patent
Vardi et al.

(10) Patent No.: US 10,973,495 B2
(45) Date of Patent: Apr. 13, 2021

(54) SYSTEM AND METHOD FOR DETERMINING PHYSIOLOGICAL CONDITIONS BASED ON VARIATIONS IN BODY TEMPERATURE

(71) Applicant: TEMPDROP LTD., Kfar Saba (IL)

(72) Inventors: Michael Vardi, Herzliya (IL); Laurent Boue', Petah-Tikva (IL)

(73) Assignee: Tempdrop LTD., Ramat Hasharon (IL)

( * ) Notice: Subject to any disclaimer, the term of this patent is extended or adjusted under 35 U.S.C. 154(b) by 138 days.

(21) Appl. No.: 16/069,544

(22) PCT Filed: Jan. 11, 2017

(86) PCT No.: PCT/IL2017/050033
§ 371 (c)(1),
(2) Date: Jul. 12, 2018

(87) PCT Pub. No.: WO2017/122199
PCT Pub. Date: Jul. 20, 2017

(65) Prior Publication Data
US 2019/0021701 A1    Jan. 24, 2019

Related U.S. Application Data

(60) Provisional application No. 62/277,508, filed on Jan. 12, 2016, provisional application No. 62/277,505, filed on Jan. 12, 2016.

(51) Int. Cl.
*A61B 10/00* (2006.01)
*A61B 5/01* (2006.01)
(Continued)

(52) U.S. Cl.
CPC ........ *A61B 10/0012* (2013.01); *A61B 5/0008* (2013.01); *A61B 5/01* (2013.01);
(Continued)

(58) Field of Classification Search
CPC ... A61B 10/0012; A61B 5/742; A61B 5/4857; A61B 5/02055; A61B 5/0008;
(Continued)

(56) References Cited

U.S. PATENT DOCUMENTS 161,921 A1    7/2007    Rausch
149,065 A1    5/2014    Pompei
(Continued)

FOREIGN PATENT DOCUMENTS

WO    WO 2006/104480    10/2006
WO    WO-2006104480 A1 * 10/2006    ........... A61B 5/0008

OTHER PUBLICATIONS

International Search Report of PCT Application No. PCT/IL2017/050033 dated Apr. 24, 2017.
(Continued)

*Primary Examiner* — Catherine M Voorhees
(74) *Attorney, Agent, or Firm* — Pearl Cohen Zedek Latzer Baratz LLP

(57) ABSTRACT

The invention is related to a system and method for determining a physiological condition. The system includes a processor configured to receive, from a first sensor, skin temperature measurements during a first period of time, wherein the first sensor is detachably and thermally coupleable to a user's skin, receive from a second sensor, measurements of ambient temperature during the first period of time, adjust the skin temperature measurements received from the first sensor using the ambient temperature measurements received from the second sensor to reduce ambient influence, receive one or more stored temperature measurements measured for at least a second time period, calculate representative temperature information for the first period of time based on the adjust skin temperature measurements from the first period of time and stored tempera- (Continued)

ture measurements and display the representative temperature information.

15 Claims, 4 Drawing Sheets

(51) Int. Cl.
 *A61B 5/00* (2006.01)
 *A61B 5/0205* (2006.01)
 *A61B 5/024* (2006.01)
 *A61B 5/145* (2006.01)
(52) U.S. Cl.
 CPC ........ *A61B 5/02055* (2013.01); *A61B 5/4857* (2013.01); *A61B 5/742* (2013.01); *A61B 5/024* (2013.01); *A61B 5/14542* (2013.01); *A61B 5/6801* (2013.01); *A61B 2010/0019* (2013.01); *A61B 2010/0029* (2013.01); *A61B 2560/0252* (2013.01); *A61B 2560/045* (2013.01); *A61B 2560/0412* (2013.01); *A61B 2562/0219* (2013.01)
(58) Field of Classification Search
 CPC . A61B 5/01; A61B 5/6801; A61B 2560/0412; A61B 2560/045; A61B 2562/0219; A61B 2560/0252; A61B 2010/0029; A61B 5/14542; A61B 5/024; A61B 2010/0019
 See application file for complete search history.

(56) References Cited

U.S. PATENT DOCUMENTS

| 8,834,389 | B2* | 9/2014 | Schafer | A61B 10/0012 |
| | | | | 600/551 |
| 2005/0245839 | A1* | 11/2005 | Stivoric | A61B 10/0012 |
| | | | | 600/549 |
| 2008/0300819 | A1* | 12/2008 | Koch | G01K 1/16 |
| | | | | 702/131 |
| 2009/0234200 | A1 | 9/2009 | Husheer | |
| 2016/0055420 | A1* | 2/2016 | Karanam | A61B 5/165 |
| | | | | 700/52 |
| 2016/0213354 | A1* | 7/2016 | Levin | A61B 5/7275 |

OTHER PUBLICATIONS

European Search Report of Application No. EP17738283.5 dated Jun. 12, 2019.

* cited by examiner

SYSTEM AND METHOD FOR DETERMINING PHYSIOLOGICAL CONDITIONS BASED ON VARIATIONS IN BODY TEMPERATURE

CROSS-REFERENCE TO RELATED APPLICATIONS

This application is a National Phase Application of PCT International Application No. PCT/IL2017/050033, International Filing Date Jan. 11, 2017, claiming priority of U.S. Provisional Patent Applications No. 62/277,505, filed Jan. 12, 2016, and No. 62/277,508, filed Jan. 12, 2016, which are hereby incorporated by reference.

BACKGROUND OF THE INVENTION

Body temperature is a valuable indicator of numerous physiological conditions. Therefore, measuring body temperature is one of the available tools for assessing physiological conditions. However, accurate measurements of core body temperatures or good approximation of core body temperatures are usually available only at a clinical facility or a research center, most common are rectal or esophageal temperature sensors. A recent research showed that measuring a temperature of the body skin below the armpit for a time period of at least 12 minutes, when the arm is tightly closed to the side of the body, is the best approximation to the core body temperature (i.e., the temperature of the inner organs of the body) than other standard temperature measuring methods tested in that research.

Accurate measurements of the body temperature can identify and helps to diagnose and/or prevent several physiological conditions. Taking multiple temperature measurements over a long period of time using traditional thermometers is complicated and inaccurate. Furthermore, each human being has its own typical body temperature variation and patterns.

Thus, there is a need to monitor body temperature automatically for long periods of time and to study typical body temperature patterns for each individual, to allow detecting deviations from the typical/normal patterns that may indicate a change in the physiological condition of that individual.

SUMMARY OF THE INVENTION

Embodiments of the invention are related to a method of determining a physiological condition and a user-specific body temperature. The method may include receiving, from a first sensor, skin temperature measurements during a first period of time, wherein the first sensor is detachably and thermally couple-able to a user's skin and receiving from a second sensor, measurements of ambient temperature during the first period of time. In some embodiments, the method may further include adjusting the skin temperature measurements received from the first sensor using the ambient temperature measurements received from the second sensor to reduce ambient influence and receiving one or more stored temperature measurements measured for at least a second time period. In some embodiments, the method may further include calculating representative temperature information for the first period of time based on the adjusted skin temperature measurements from the first period of time and the stored manipulated skin temperature measurements and displaying the representative temperature information.

Other embodiments of the invention are related to a system for determining a physiological condition and a user-specific body temperature. The system may include a processor and a memory to store thereon instructions to be carried by the processor. The instructions may include receiving, from a first sensor, skin temperature measurements during a first period of time, wherein the first sensor is detachably and thermally coupleable to a user's skin and receiving from a second sensor, measurements of ambient temperature during the first period of time. In some embodiments, the instructions may further include adjusting the skin temperature measurements received from the first sensor using the ambient temperature measurements received from the second sensor to reduce ambient influence and receiving one or more stored temperature measurements measured for at least a second time period. In some embodiments, the instructions may further include calculating representative temperature information for the first period of time based on the adjusted skin temperature measurements from the first period of time and the stored temperature measurements and displaying the representative temperature information.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figures 1A, 1B, 1C:
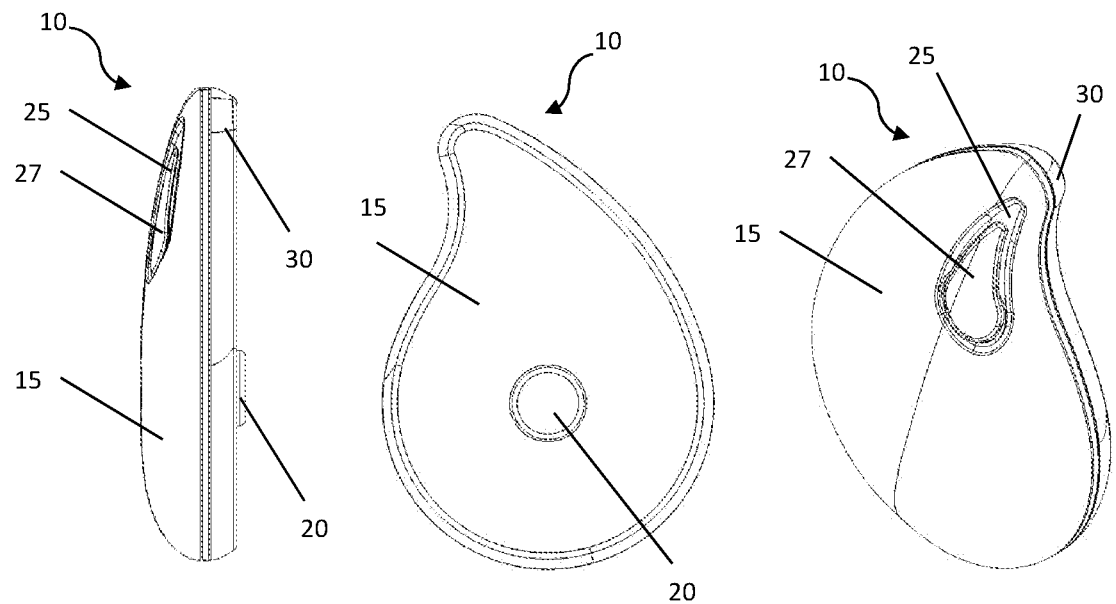
FIGS. 1A-1C includes illustrations of several views of a device for measuring skin temperatures according to some embodiments of the invention.
Figure 1D:
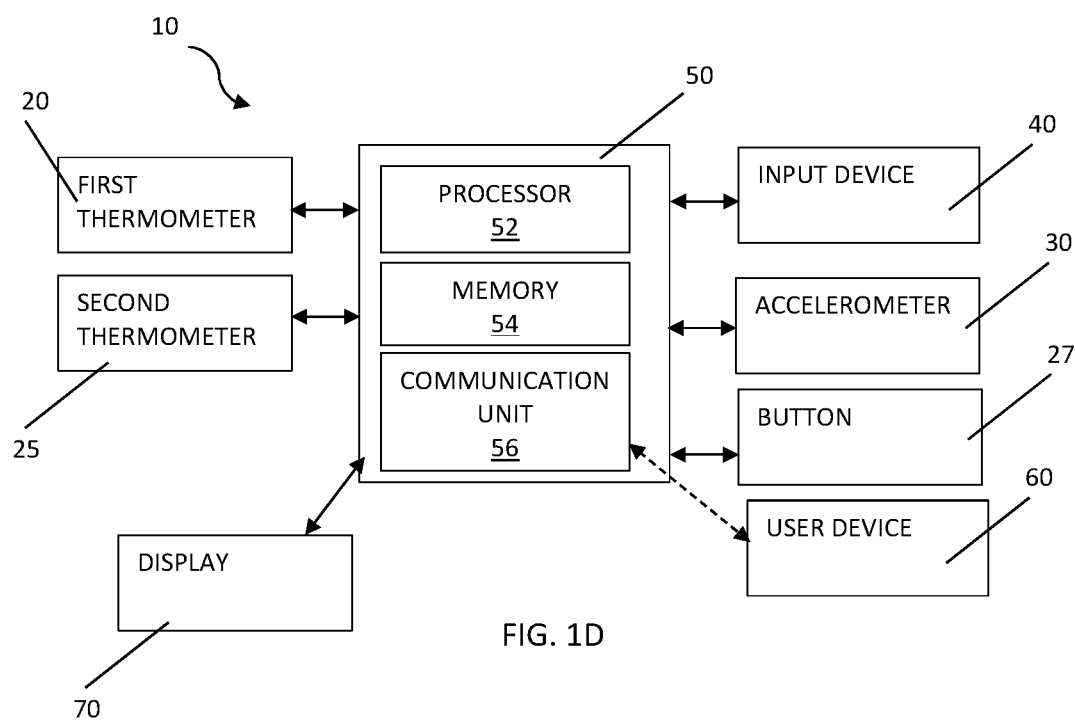
FIG. 1D is a high level block diagram of the device for measuring skin temperatures according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "predicting", "calculating," "determining", "establishing", "analyzing", "checking", "manipulating", "filtering" or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Some embodiments of the invention are related to a system and method for determining a physiological condition based on substantially continuous and/or repetitive skin temperature measurements. In some embodiments, the skin temperature measurements may be nonconsecutive, for example, measured over 3 hours during a first night's sleep and for 3 more hours during a second night's sleep. A device for measuring body temperature according to embodiments of the invention may include a first temperature sensor (e.g., a thermistor) to be thermally coupled to the skin of a user, for example, under or close to the armpit. The device may be a wearable device that can be carried by the user, for example, be worn around the upper arm of the user, such that the temperature sensor is attached to the skin of the user. The device may further include a second temperature sensor to measure ambient temperature. According to some embodiments, the device may further include an accelerometer (e.g., a 3-axis accelerometer) to track movements, for example, movement of the user's arm. A system and method according to embodiments of the invention may use measurements from the second temperature sensor and/or the accelerometer to reduce undesired influences from the measured skin temperatures. The system and method may further save for each user the measured body temperature and manipulated skin temperatures and may conduct a learning process to each user, for example, by identifying typical temperature patterns/characteristics for each user at different times of day, month etc.

Reference is now made to FIGS. 1A and 1B which are illustrations and a block diagram of a device for measuring a user-specific body temperature according to some embodiments of the invention. FIGS. 1A-1C show side, bottom and top view of a wearable device 10. Device 10 may include a housing 15 for holding a first temperature sensor 20 and a second temperature sensor 25. Housing 20 may further hold an accelerometer 30. Device 10 may further include an attachment element (not illustrated) for attaching housing 15 to the skin of a user. Attachment element may include an elastic band, a sticker, a sleeve or the like. Device 10 may be attached to one the user's limbs, preferably closest to the torso such as the armpit, genitals, or any body part for measuring skin temperature. Device 10 may further include additional one or more input devices 40. Input device 40 may include, for example: a piezoelectric sensor, a photoelectric sensor, a heart rate sensor, a microphone, a bio-impedance sensor, and/or conductivity sensor. In some embodiments, device 10 may include a display 70 and a button 27.

In some embodiments, first temperature sensor 20 is detachable and thermally coupled to the skin of the user. First temperature sensor 20 may be attached and thermally coupled to the skin at all time while the user is wearing/using device 10, for example, during sleeping hours. Regardless of the position of the user body part carrying device 10, e.g., the arm, the leg, the forehead, etc. the attachment element of device 10 keeps temperature sensor 20 attached and thermally coupled to the skin. Temperature sensor 20 may be configured to measure and collect skin temperature.

In some embodiments, ambient temperature sensor 25 may be configured to measure and collect ambient temperature in the close environment of device 10. For example, when device 10 is worn around the arm temperature sensor 25 may measure the axillary (armpit) temperature when the arm is close and adjacent to the user's torso for long period of time, often occurring during sleep. In such case the temperature measured by temperature sensor 25 may be closer to the temperature measured by temperature sensor 20 than temperature measured when the arm is raised. In another case when the arm is raised, ambient temperature measured and collected by temperature sensor 25 (e.g., during sleeping) may collect ambient temperature, for example, the room temperature, the ambient temperature between a blanket covering the user and the user's torso, the temperature in proximity of the user's body between clothing worn by the user and the body of the user, etc.

In some embodiments, accelerometer 30 may measure movements of device 10, for example, the arm movements. Accelerometer 30 may be any accelerometer known in the art, for example, a MEMS device. In some embodiments, accelerometer 30, and temperature sensors 20 and 25 may all be in communication with a controller 50 of device 10, illustrated in FIG. 1B. Accelerometer 30, and temperature sensors 20 and 25 may send collected data to be processed by controller 50.

In some embodiments, controller 50 may include a processor 52 (e.g., a chip), a memory 54 and a communication unit 56. Memory 54 may include a Random Access Memory (RAM), a read only memory (ROM), a Dynamic RAM (DRAM), a Synchronous DRAM (SD-RAM), a double data rate (DDR) memory chip, a Flash memory, a volatile memory, a cache memory, a buffer, a short term memory unit, a long term memory unit, or other suitable memory units or storage units. Memory 54 may store one or more executable codes to be executed by processor 52, for example, codes for receiving temperature measurements data from temperature sensors 20 and 25, receiving acceleration data from accelerometer 30. The code may further include manipulating the measurements from temperature sensor 20 using measurements from temperature sensor 25 and accelerometer 30. The code may include receiving additional data from one or more input devices 40. The code may include sending and receiving information and/or instructions from a user device 60 or from any other external computing device via communication unit 56.

In some embodiments, communication unit 56 may be configured to communicate with user device 60 (e.g., a smart phone, a tablet, a smartwatch, a laptop, a PC, etc.) or any external computing device, using any known protocol, for example, Bluetooth, Wi-Fi, and the like. In some embodiments, memory 54 may store identification information of wearable device 10 to be recognized by user device 60 when establishing the communication. In some embodiments, user device 60 may further include one or more sensors for providing additional data, for example, a temperature sensor for measuring room temperature, a microphone that may provide data on sleep quality, such as snoring or interfering noise, a light sensor, barometer, humidity sensor and the like. In some embodiments, device 10 may be configured to communicate with user device 60 following a press of button 27, by the user. Is other embodiments accelerometer 30 may be configured to initiate the communication by shaking device 10 or perform some tactile tapping sequence.

Figure 2:
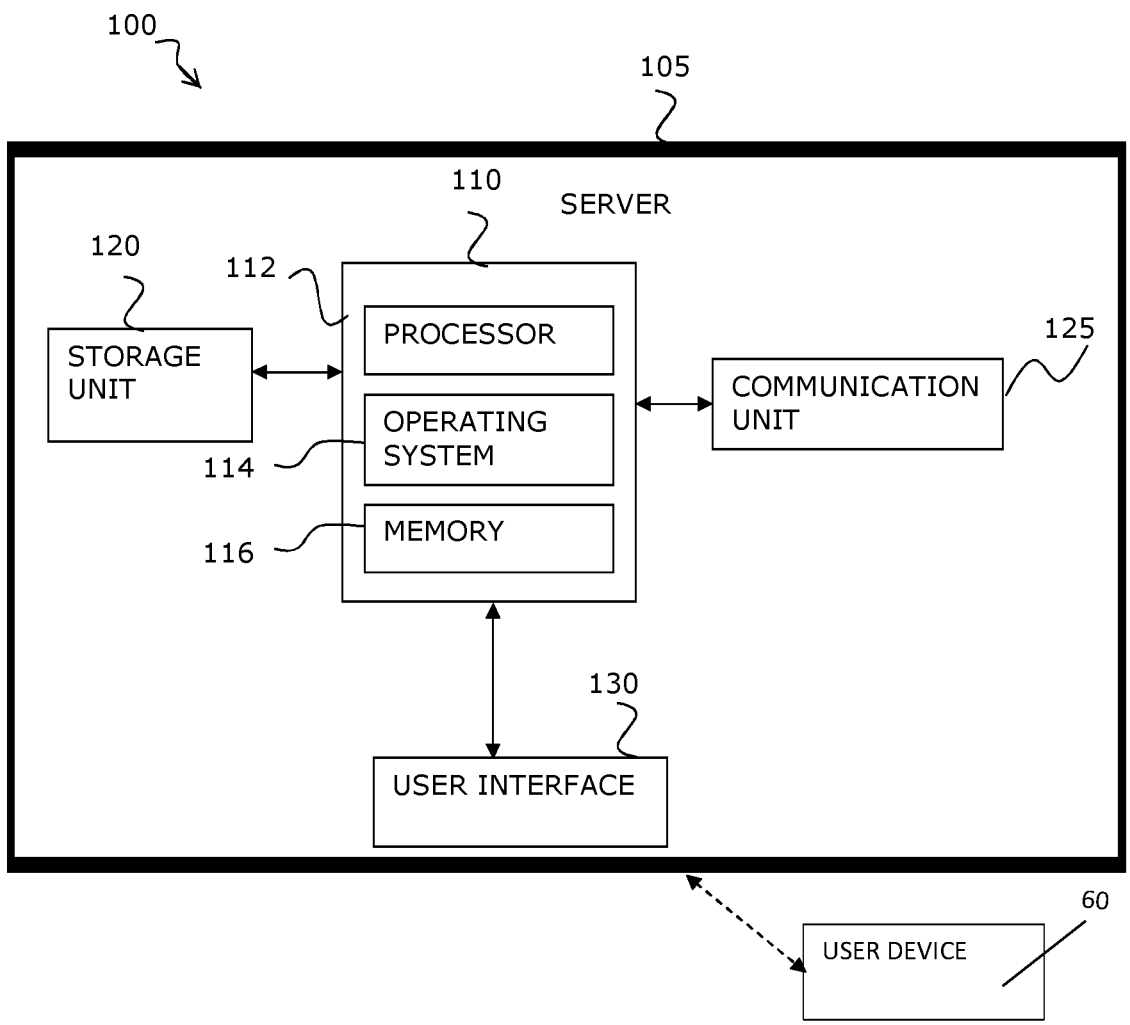
FIG. 2 is a high level block diagram of a system for determining a physiological condition and user-specific body temperature according to some embodiments of the invention.

Reference is now made to FIG. 2 which is a high level block diagram of a system for determining a physiological condition according to some embodiments of the invention. A system 100 maybe include a server 105 that may be, for example, a cloud base server or a physical processing unit. Server 105 may include processing device 110, a storage unit 120, a user interface 130 and a communication unit 125. Processing unit 110 may include a processor 112 that may be, for example, a central processing unit (CPU), a chip or any suitable computing or computational device, an operating system 114 and a memory 116. Processor 112 may be configured to carry out methods according to embodiments of the present invention by for example executing instructions stored in a memory such as memory 116. Operating system 114 may be or may include any code segment designed and/or configured to perform tasks involving coordination, scheduling, arbitration, supervising, controlling or otherwise managing operation of processing device 110, for example, scheduling execution of programs. Operating system 114 may be a commercial operating system. Memory 116 may be or may include, for example, a Random Access Memory (RAM), a read only memory (ROM), a Dynamic RAM (DRAM), a Synchronous DRAM (SD-RAM), a double data rate (DDR) memory chip, a Hash memory, a volatile memory, a non-volatile memory, a cache memory, a buffer, a short term memory unit, a long term memory unit, or other suitable memory units or storage units. Memory 116 may be or may include a plurality of, possibly different memory units.

Memory 116 may store any executable code, e.g., an application, a program, a process, task or script. The executable code may include codes for determining a physiological condition or any other codes or instruction for executing methods according to embodiments of the present invention. The executable code may be executed by processor 112 possibly under control of operating system 114.

Storage 120 may be or may include, for example, a hard disk drive, a floppy disk drive, a Compact Disk (CD) drive, a CD-Recordable (CD-R) drive, a universal serial bus (USB) device or other suitable removable and/or fixed storage unit. Content, such as historical temperature measurements, may be stored in storage 120 and may be loaded from storage 120 into memory 116 where it may be processed by processor 112.

User interface 130 may be or may include any device configured to receive inputs from a user (e.g., an administrator) and display outputs to the user. For example, user interface 130 may include, a screen, a keyboard, a pointing device, an audio device, or any applicable input/output (I/O) devices may be connected to processing unit 110.

Communication unit 125 may include any wired or wireless network interface card (NIC) that may allow processing unit 110 to communicate with external devices such as user device 60 and/or wearable measurement device 10, for example, over the internet.

In some embodiments, server 105 may further receive other information from remote database (not illustrated). The remote databases may be in communication with various sensors such as room temperature sensors, humidity sensors, etc. Example, for such sensor may include a "smart" thermometer like the NEST©, Sense device by Hello, or any other device that may include a sensor, an internet connectivity and a remote database. The other information may also be received from public databases, such as weather report databases etc.

Figure 3:
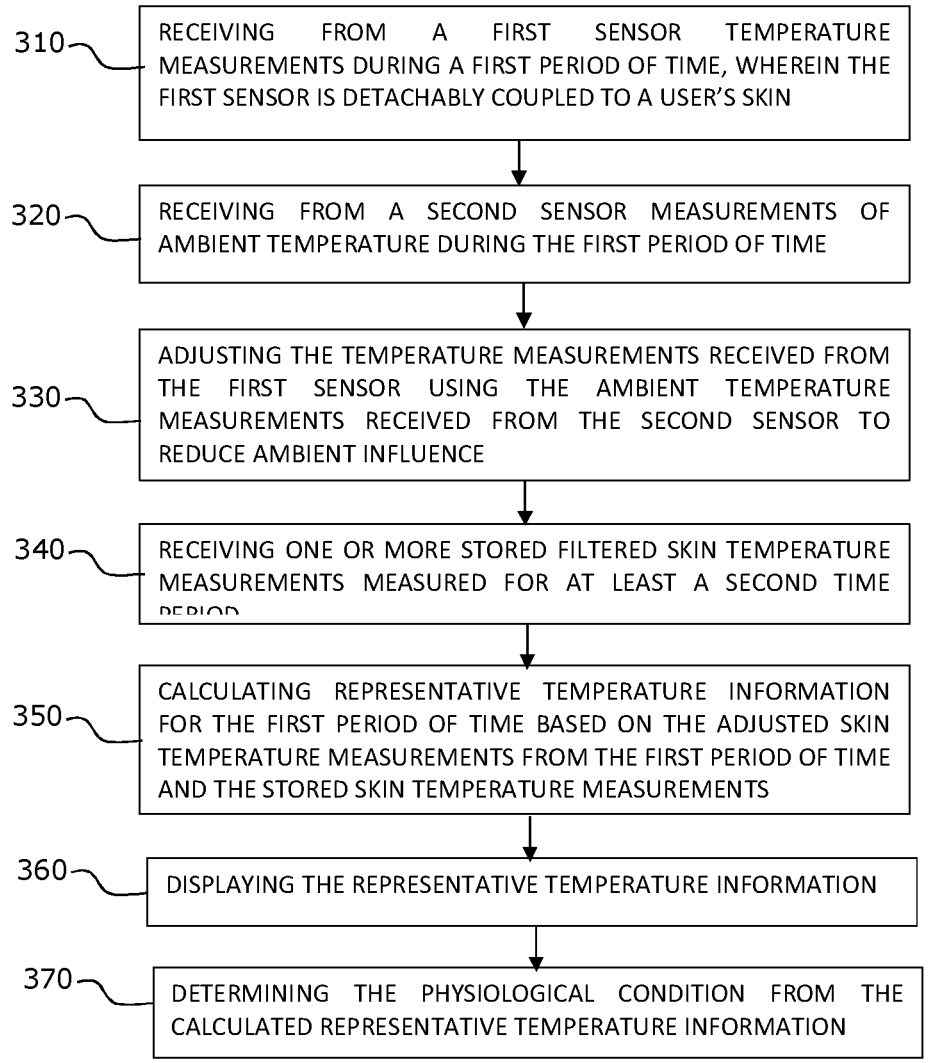
FIG. 3 is a flowchart of a method of determining a physiological condition according to some embodiments of the invention.

Reference is now made to FIG. 3 which is a flowchart of a method of determining a physiological condition according to some embodiments of the invention. The method of FIG. 3 may be conducted by processor 112 of server 105 and or processor 52 of system 100 and device 10. In operation 310, embodiments include receiving from a first sensor skin temperature measurements during a first period of time, wherein the first sensor is detachably and thermally coupleable to a user's skin. First sensor 20 may send (e.g., every second, every minute, when a button 27 is pressed by a user, etc.) skin temperature measurements to processor 52 and/or to processor 112. In some embodiments, the first period of time may be several minutes, several hours, overnight, during sleeping time, one day, a week, a month etc.

In operation 320, embodiments include receiving from a second sensor measurements of ambient temperature during the first period of time. Second sensor 25 may send (e.g., every second, every minute, etc.) ambient temperature measurements to processor 52 and/or to processor 112. For example, when device 10 is worn under the arm of the user and the user is in bed covered by a blanket, sensor 25 may measure the temperature between the arm and the user's body, when the arm lays close to the body or a temperature under the blanket, otherwise.

In operation 330, embodiments may include adjusting the skin temperature measurements received from the first sensor using the ambient temperature measurements received from the second sensor to reduce ambient influence. Processor 52 and/or processor 112 may compare the measurements from first sensor 20 and second sensor 25 and define time intervals in the first period at which the skin temperature is less influenced by the ambient temperature, for example, when the difference between the two measurements (at the same time) is smaller than a threshold value or that the ratio between the two measurements is smaller than a threshold value. In some embodiments, manipulating the skin temperature measurements may include, filtering undesired measurements, extrapolating between skin temperature measurements, integrating, differentiating, or any mathematical manipulation that may be applied to time dependent temperature measurements known in the art. In some embodiments, in order to define periods at which the ambient conditions may have influence on the measurements received from the skin temperature sensor, a skin temperature measurement and an ambient temperature measurement taken at the same day/night time (in the past, for example between 02:00-04:00 AM) may be compared. In some embodiments, if the difference between the two is larger than a threshold value, the skin temperature measurement is identified as "influenced by the ambient temperature".

Period of time at which the difference between the skin and ambient temperature measurements is larger than a threshold value may occur when device 10 is subjected to the environment, for example, when the user raises his arm. In such case the skin in contact with device 10 may cool down (when environment is colder than the user's body temperature) and the measured skin temperature may be "influenced by the ambient temperature". Processor 52 and/or processor 112 may select to filter from the skin temperature measurements, measurements having an ambient ° influence higher than a predetermined threshold, for example, $0<\Delta T<0.5°$ C. may be considered low influence and, $0.5<\Delta T<1°$ C. may be considered medium influence and $1°$ C.$<\Delta T$ and be considered high influence.

In some embodiments, analyzing the rate of changes in the measured skin and/or ambient temperatures may allow to study the ambient influence. The outcome of the analysis may be used in further manipulation of the measured skin temperature. For example, the rate of change in the measured skin and/or ambient temperature may very when the user raised his hand in a relatively cold room than in a warmer room.

In some embodiments, the method may include receiving from an accelerometer, measurements, during the first period of time. In some embodiments, the accelerometer may be coupled to at least one of the first sensor and the second sensor, for example, included in device 10. Accelerometer 30 may send processor 52 and/or processor 112 acceleration measurements. In some embodiments, the method may include further adjusting (e.g., filtering noise) from the skin temperature measurements, based on the measured acceleration. Processor 52 and/or processor 112 may identify from the acceleration measurements time intervals in the first period at which device 10 was moving at movements higher than a predetermined threshold. Processor 52 and/or processor 112 may manipulate skin measurements taken during the identified time intervals from the skin temperature measurements. In some embodiments, movements of the user wearing device 10 may be identified by a change in the distance between device 10 and user device 60 (e.g., the user's mobile phone). The transceivers in each device may detect a decline in the intensity of a received signal as the distance increases.

In some embodiments, the method includes manipulating the skin temperature measurements, based on data received from one or more input devices. The manipulation may include filtering skin temperature measurements that may be inaccurate due to some external influence such as ambient temperature, other ambient conditions, personal/individual parameters such as a medical condition of the user, and the like. For example, when the user wakes up, the user is a restless sleeper, or the user is sick. For example, the input device may be or may include a light sensor and the received data may include light intensity measurements that may indicate if the measurements are taken during the night or the day. In another example, the input device may be a heartrate sensor and the received data may include an increase in the heartrate that may indicate that the user woke up. In yet another example, the input device is the smartphone's microphone that may give an indication about sleeping quality, sleep apnea events, snoring, noise disturbances etc.

In yet another example, the input device may be oxygen saturation sensor and the received data may include oxygen saturation, indicating the medical condition of the user. Processor 52 and/or processor 112 may receive from one or more input devices 40 one or more inputs. For example, device 40 may be a heartrate sensor, oxygen saturation sensor, a piezoelectric sensor, photoelectric sensor, bio-impedance sensor (electrical skin conductivity), acidity sensor, a humidity sensor, a light sensor, a microphone and the like that is included or in communication with device 10 and processor 52 and/or processor 112 may filter or manipulate temperature measurements using heartrate measurements and/or oxygen saturation measurements.

In some embodiments, the method may include receiving from a user computing device user related data and manipulating the temperature measurements (e.g., skin temperature measurements, body temperature, manipulated skin temperature measurements, ambient, etc.) using the user related data. Processor 52 and/or processor 112 may receive from user device 60 and/or an external data base (e.g., storage unit 120 or other) user related data, for example, age, gender, weight, height and a medical condition (e.g., PCOS—Polycystic ovary syndrome). The user may log into an application on user device 60 and may enter the user related data. For example, processor 52 and/or processor 112 may receive information that the user is a 30 years old woman, accordingly, processor 52 and/or processor 112 may look for a bi-phasic temperature patterns overtime in the manipulated temperatures (e.g. skin temperature, body temperature or temperature information) for determining the menstrual cycle circadian pattern or further manipulating the temperature data thereof. The user related data may further include subjective information recited from the user, for example, a subjective assessment of the user reading his/hers medical condition or feeling. For example, a woman using device 10 may fill an online questionnaire running on device 60 regarding her current menstrual condition: e.g., bleeding, spotting, mild bleeding, medium bleeding and heavy bleeding.

In operation 340, embodiments may include receiving one or more stored temperature measurements measured for at least a second time period. Processor 52 and/or processor 112 may receive from memory 54 and/or storage unit 120 historical temperature measurements taken for the user for example, during one or more hours, a day, a week, a month, the same hours in two or more different days, and several months (e.g., during 9 month of pregnancy) and the like. The historical temperature measurements (e.g., skin temperature measurements, ambient temperature measurements, manipulated temperature measurements, body temperature measurements etc.) may be stored in memory 54 and/or storage unit 120 and associated with specific user (e.g., using ID, personal code and the like).

In some embodiments, historical data stored for a specific user may include acceleration measurements received from accelerometer 30 and/or measurements received from one or more input devices 40. In some embodiments, the historical data may include historical calculated representative temperature information. In some embodiments, the historical data may include a user related data.

In operation 350, embodiments include calculating representative temperature information for the first period of time based on the adjusted skin temperature measurements from the first period of time and the stored temperature measurements. In some embodiments, processor 52 and/or processor 112 may calculate an initial representative temperature information using only the adjusted skin temperature measurements from the first period of time. For example, the adjusted skin temperature measurements from the first period of time may be used to calculate an average temperature, identify, for example, the lowest/highest or median temperature for the adjusted skin temperature measurements from the first period of time, and the like. In some embodiments, the initial representative temperature information may include a calculated pattern taken from the adjusted skin temperature measurements from the first period of time. In some embodiments, the initial representative temperature information may be stored in memory 54 and/or storage unit 120, for further use. In some embodiments, at least some of the representative temperature information collected for the user may be stored in memory 54 and/or storage unit 120.

In some embodiments, during the calculation of the initial representative temperature information, different parameters (e.g., measurements) may be given different weights (e.g., coefficients) according to their impotence and influence. For example, the ambient temperature measurements may be given higher weight than a sound measurements due to the higher influence of the ambient temperature on the skin temperature. In yet another example, if the ambient temperature is lower than a predefined threshold (e.g., when the blanket was dropped during the night) an increase in the difference between the ambient and the skin temperature may be detected and the weight of the ambient temperature measurements may be reduced. The weights may vary from user to user according for example, on the age, gender, location, etc. The weights (e.g., coefficients) may be updated in time as more measurements and representative temperature information is collected and stored for each user.

Figure 4A:
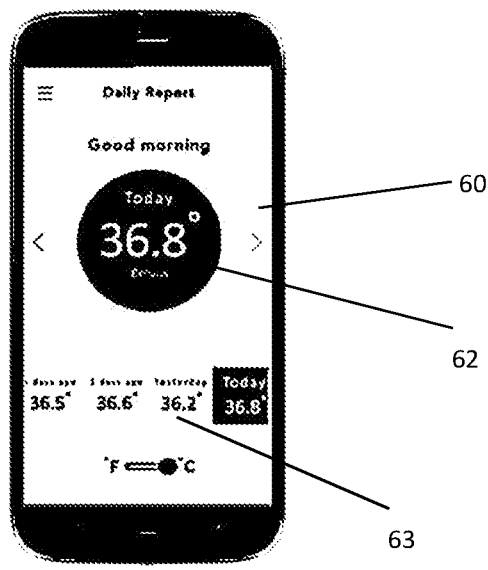
FIGS. 4A and 4B are illustrations of displays of representative temperature information according to some embodiments of the invention.

In some embodiments, calculating representative temperature information may further be based on historical data for the specific user (e.g., stored in memory 54 and/or storage unit 120) and/or the user related data. In some embodiments, the representative temperature information is a value representing of the user's body temperature during the first period of time, as illustrated in FIG. 4A. A single value 62 may be presented on display 60. In some embodiments, other values 63, for example, from previous days and/or the second period of time may also be presented. For example, the representative temperature information may include an average temperature of all the manipulated measured skin temperature and a stored manipulated skin temperature from the same day of two or more consecutive months. In yet another example, the representative temperature information may be a comparison (e.g., the difference) between a mathematical value (e.g., minimum, maximum, average, maiden etc.) taken from the manipulated measured skin temperature and the stored manipulated skin temperature.

Figure 4B:
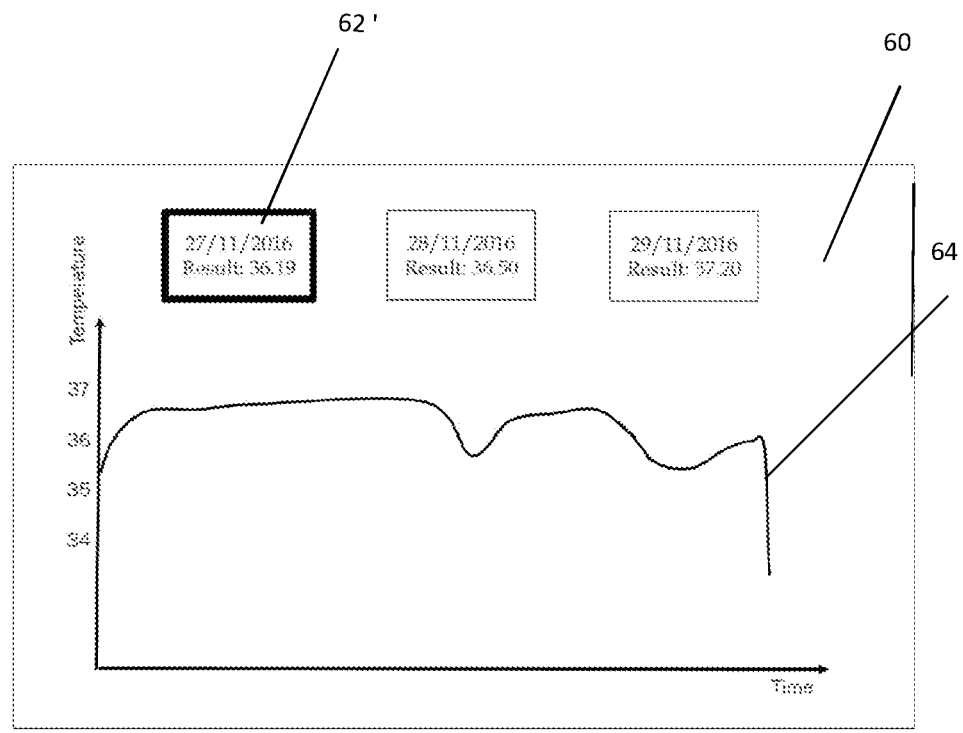

In some embodiments, the representative temperature information is a representative temperature pattern, as illustrated in FIG. 4B. A pattern 64 may be presented on display 60, optionally with one or more single values 62'. For example, pattern 64 may include adjusted temperature measurements taken during sleeping hours and single value 62 may be the average of all the adjusted temperature measurements. In yet another example, pattern 64 may include average temperature measurements form sleeping hours during a month and single value 62 may be average temperature at a specific day. In some embodiments, the method includes identifying typical patterns in the manipulated skin temperature from the second period of time. For example, processor 52 and/or processor 112 may identify skin temperature measurements patterns at substantially the same hours during sleeping time at each night during the past 3 month. In some embodiments, the method includes calculating the representative temperature information is also based on the typical patterns, for example, taking the identified pattern measured during the first period of time as the representative temperature information.

In operation 360, embodiments include displaying the representative temperature information. Processor 52 and/or processor 112 may display the representative temperature information to the user, for example, on a screen of user device 60, as illustrated in FIGS. 4A and 4B and/or on display 70 included in device 10. Additionally or alternatively, processor 52 and/or processor 112 may display the representative temperature information to other users, for example, to a care giver of the user when the user is an elderly man/woman, to a medical service provider (e.g., the personal physician of the user) and the like.

Additionally or alternatively to operation 360, in operation 370, embodiments may include determining the physiological condition from the calculated representative temperature information. In some embodiments, operation 370 may be performed by processor 52 and/or processor 112 or may be performed by an external processor. The external processor may receive from device 10 and/or system 100 the calculated representative temperature information. The external processor may be configured to determining the physiological condition based on the calculated representative temperature information. In some embodiments, the external processor may be configured to display to the user, for example, on user device 60, the determined physiological condition. In some embodiments, determining the physiological condition may further be based on the user related data In some embodiments, the user related data may be received from external sources via the internet. The external sources may include external database, for example, medical records from medical service providers, applications the user is using and the like. In some embodiments, the external sources may include applications installed on a user's mobile device. The user may switch between software applications after using them for a period of time to find the best suited software application based on the user's personal preferences. Accordingly, the user related data may be stored in several different databases using different scales and formats. Some of these applications may have similar usage/features/indications, such as, ovulation calendars and fertility tracking applications.

In some embodiments, processor 52 and/or processor 112 may process and normalize the user related data received from external sources in order to have the data at a unified format. For example, processor 52 and/or processor 112 may normalize time, date and temperature scale for all temperature measurements received for a specific user, for example, form his medical files from the local clinic, hospital medical files and measurements taken using device 10. The processor may plot all the temperature data on a single plot.

In yet another example, subjective values given by the user and/or a caregiver in two or more medical data related applications, using two or more scales can be normalized into a single scale. For example, the user may use a pain scale of 1-10 to evaluate his pain level using a first application and a nurse treating the user may evaluate his pain using a 1-6 pain scale at a second application. In such case processor 52 and/or processor 112 may normalize both scales to a single scale. Another example of such normalization is to perform a linear interpolation as follows:

A first mobile or desktop application, App1, enables its users to input grads ranging from 1 to 4 and a second desktop application, App2, enables to input grads in a range of 1 to 16 (for the same quantity, and the same question/issue).

Processor 52 and/or processor 112 may further be configured to bring all the data to a common range, for example a range of 1 to 10.
For example, denote by "g1" the grade according to App1 and "g2" the grade according to App2. Both can be brought to a common grading denoted "CmnGR" by equations 1 and 2.

$$\text{CmnGR}=10*g1/4 \text{ (for App1; if } g1=2, \text{ we get CmnGr=5)} \quad (1)$$

$$\text{CmnGR}=10*g2/16 \text{ (for App2; if } g1=8, \text{ we also get CmnGr=5)} \quad (2)$$

In some embodiments, the interpolation may not have to be linear and specific coefficients may be assigned to each grad, for example, when the grades of one application are not well spread out between themselves. For example, if there are many grades corresponding to high scores in first app and relatively few corresponding to low scores in second application.

In some embodiments, processor 52 and/or processor 112 may analyze the user related data received from external sources using additional information. The additional information may include, the type of electronic device used by the user to extract the measurements, whether they were taken using a smartphone or an adaptive device. The type of smartphone may also be taken into account. The user may input free text to user device 60, to be sent to processor 52 and/or processor 112. Processor 52 and/or processor 112 may normalize the free text inputted by the user in order to unify the input from various users using various software mobile applications having different user interfaces and menus. The set of rules upon which the normalizations are performed may change from time to time and may change according to the various user interface and input methods of different mobile applications. For example if a woman is logging various physiological parameters related to a female menstrual cycle such as: cervical mucus properties and appearance, menses, cervix orientation, mood, food cravings etc. Different applications may provide various interfaces and/or menus to track the menses' flow, color etc.

In some embodiments, the user related data may include physiological data of a mature (e.g., 30 years old) female and the calculated representative temperature information includes representative temperature values each determined based on manipulated skin temperature measurements taken during sleeping hours in at least 30 days and the physiological condition is the menstrual cycle. For example, a woman's menstrual cycle exhibits a typical bi-phasic temperature pattern: low sleeping body temperatures in the pre-ovulatory phase and higher body temperatures caused by increased Progesterone secretion in the post-ovulatory phase. Processor 52 and/or processor 112 or the external processor may identify a sharp decline in body temperature in the minimum or average manipulated skin temperature in a particular day during the month and may determine the ovulation day based on the sharp decline (e.g., of at least 0.2-0.5° C.). In addition, the system may identify a characteristic temperature pattern over a few days prior to the expected/predicted temperature shift based on monthly temperature patterns identified by the system.

In some embodiments, the first period of time may be 9 month of a pregnancy and the manipulated temperature measurements are compared to manipulated temperature measurements taken during previous pregnancy(s) (e.g., the second period of time) and the physiological condition is the overall wellbeing of the pregnant woman.

In some embodiments, the calculated representative temperature information is the maximum or minimum measured skin temperature during a measuring period and the physiological condition is at least one of a fever and hypothermia (e.g., in elderly people). In some embodiments, the calculated representative temperature information occurs in a duration at which the measured skin temperature is above a predetermined value and the physiological condition is dehydration. For example, if the duration at which the measured skin temperature is above 37.5° C. (but below 38° C.) for a person having normally 36.8° C., is more than 4 hours, that may indicate that the person is dehydrated.

In some embodiments, determining the physiological condition from the calculated representative temperature information may further include receiving (e.g., from storage using 120) calculated representative temperature information and/or manipulated skin temperature measurements stored for a plurality of users. Processor 52 and/or processor 112 may analyze the stored calculated representative temperature information and/or manipulated skin temperature measurements of the plurality of users to identify information/patterns that may assist in determining the user's current physical condition. For example, the information may indicate when the movement of the user has no influence on the maximum temperature measured during a fever. Accordingly, processor 52 and/or processor 112 may not manipulate skin temperature measurements using the acceleration measurements.

In some embodiments, the user may further be clustered to one or more specific groups and the plurality of users may be selected to be included in one or more of the specific groups. For example, the user may be cluster to a sub-group of mature women ages 20-40, in their postpartum phase, women with PCOS or other hormonal pathologies, elderly men/women ages 70-90, restless sleepers and the like.

In some embodiments, the method may include receiving from a user computing device data related to at least one of: timetable (e.g., calendar, tasks list, etc.), a lifestyle data (e.g., sport training sessions, hobbies, activity levels, sleep quality, food and drink intake etc.) and tracking data (e.g., locations, travels) of a user. For example, processor 52 and/or processor 112 may automatically receive from user device 60, at least one of: the user's calendar, the user's tasks, time zone and location. In some embodiments, the method includes synchronizing manipulated skin temperature measurements with the data related to the timetable of the user, and wherein the representative temperature information or a physiological condition may be predicted also based on the circadian rhythm disruption caused by day-night interferences. For example, if the user travels 6 time zones East or West, or started working in night shifts, processor 52 and/or processor 112 may learn the disruption effect on the manipulated skin temperature measurements and patterns to calculate the correct representative temperature information or identify abnormal physiologies (e.g., obesity, diabetes, fertility problems and the like) that are known to be affected by disrupting user's circadian day-night cycle. For example: processor 52 and/or processor 112 may determine how changing time zones in various phases of the menstrual cycle affects ovulation day, if at all, for every user and predict physiological conditions such as ovulation which are affected by body-clock (circadian) disruption. In some embodiments, processor 52, processor 112 and/or the external processor may learn for the second period of time (e.g., monthly) temperature patterns at various conditions (night-day shift working) taking into account at least some of the manipulating and filtering methods disclosed above.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of determining a physiological condition, comprising:
    receiving, from a first sensor, skin temperature measurements during a first period of time, wherein the first sensor is detachably and thermally couple-able to a user's skin;
    receiving, from a second sensor, measurements of ambient temperature during the first period of time,
    receiving from an accelerometer, measurements, during the first period of time, wherein the accelerometer is coupled to at least one of the first sensor and the second sensor;
    adjusting the skin temperature measurements received from the first sensor using the ambient temperature measurements received from the second sensor to reduce ambient influence;
    correcting the adjusted temperature measurements based on the measured acceleration;
    receiving one or more stored temperature measurements measured and adjusted to reduce ambient influence for at least a second time period;
    calculating representative temperature information for the first period of time based on the adjusted skin temperature measurements from the first period of time and the stored temperature measurements; and
    displaying the representative temperature information.

2. The method of claim 1, further comprising:
    identifying typical patterns in the adjusted skin temperature measurements from the second period of time,
    and wherein calculating the representative temperature information is also based on the typical patterns.

3. The method of claim 1, further comprising manipulating the adjusted skin temperature measurements, based on data received from one or more input devices, wherein the one or more input devices are selected from a list consisting at least one of: a light sensor, a heartrate sensor and oxygen saturation sensor; and wherein the data received is selected from a group consisting of: measured light, time of day, heart rate, and oxygen saturation.

4. The method of claim 1, further comprising:
    receiving from a user computing device user related data; and
    manipulating the adjusted skin temperature measurements using the user related data.

5. The method of claim 4, wherein the user related data comprises at least one of: age, gender, weight, height and a medical condition.

6. The method of claim 1, further comprising:
    receiving from a user computing device data related to at least one of: a timetable, lifestyle data, and tracking data of a user; and
    manipulating the adjusted skin temperature measurements based on the data received from the user, and wherein calculating representative temperature information is also based on the manipulated skin temperature.

7. The method of claim 6, wherein the data related to a timetable is selected from a list consisting at least one of: the user's calendar, the user's tasks, moving from one time zone to another and location.

8. The method of claim 1, wherein the representative temperature information is a value representing the user's temperature during the first period of time.

9. The method of claim 1, wherein the representative temperature information is a temperature pattern.

10. The method of claim 1, wherein the first period of time is one of: sleeping hours, 12 hours, 1 day, a week and a month and the second period of time is one of: one or more hours, a day, a week, a month, the same hours in two or more different days, and several months.

11. The method of claim 1, further comprising:
    determining the physiological condition from the calculated representative temperature information.

12. The method of claim 11, wherein the calculated representative temperature information includes temperature values, each temperature value is determined based on measurements taken during sleeping hours during at least 30 days and the physiological condition is fertility.

13. The method of claim 11, wherein the calculated representative temperature information is the maximum or minimum of the representative temperature information during a first measuring period and the physiological condition is at least one of a fever and hypothermia.

14. A system for determining a physiological condition, comprising:
    a processor configured to:
        receive from a first sensor skin temperature measurements during a first period of time, wherein the first sensor is detachably and thermally coupled-able to a user's skin;
        receive from a second sensor measurements of ambient temperature during the first period of time,
        receive from an accelerometer, measurements, during the first period of time,
        wherein the accelerometer is coupled to at least one of the first sensor and the second sensor;
        adjust the skin temperature measurements received from the first sensor using the ambient temperature measurements received from the second sensor to reduce ambient influence;
        correct the adjusted temperature measurements based on the measured acceleration;
        receive one or more stored temperature measurements measured for at least a second time period;
        calculate representative temperature information for the first period of time based on the adjusted skin temperature measurements from the first period of time and the stored temperature measurements; and
        display the representative temperature information.

15. The system of claim 14, wherein the
    processor is further configured to:
        determine the physiological condition from the calculated representative temperature information.

* * * * *